United States Patent
Sunil et al.

(10) Patent No.: US 12,419,218 B2
(45) Date of Patent: Sep. 23, 2025

(54) METHODS OF MEASURING RESIDUE DURING HARVEST

(71) Applicant: AGCO Corporation, Duluth, GA (US)

(72) Inventors: Tresa Sunil, Hesston, KS (US); Russell H. Gollnick, Hesston, KS (US)

(73) Assignee: AGCO Corporation, Duluth, GA (US)

( * ) Notice: Subject to any disclaimer, the term of this patent is extended or adjusted under 35 U.S.C. 154(b) by 922 days.

(21) Appl. No.: 17/361,729

(22) Filed: Jun. 29, 2021

(65) Prior Publication Data
US 2021/0400870 A1 Dec. 30, 2021

Related U.S. Application Data

(60) Provisional application No. 63/045,308, filed on Jun. 29, 2020.

(51) Int. Cl.
| | | |
|---|---|---|
| A01D 41/127 | (2006.01) | |
| A01B 79/00 | (2006.01) | |
| A01D 41/12 | (2006.01) | |
| G01N 22/00 | (2006.01) | |
| G01N 33/00 | (2006.01) | |

(52) U.S. Cl.
CPC .......... *A01D 41/127* (2013.01); *A01B 79/005* (2013.01); *A01D 41/1243* (2013.01); *G01N 22/00* (2013.01); *G01N 33/0098* (2013.01)

(58) Field of Classification Search
CPC .............. A01D 41/127; A01D 41/1243; A01B 79/005; G01N 22/00; G01N 33/0098
USPC .................................................... 701/50
See application file for complete search history.

(56) References Cited

U.S. PATENT DOCUMENTS

| | | | |
|---|---|---|---|
| 4,637,406 | A | 1/1987 | Fell et al. |
| 5,569,081 | A | 10/1996 | Baumgarten et al. |
| 5,970,802 | A | 10/1999 | Strubbe |
| 10,292,323 | B2 | 5/2019 | Missotten et al. |
| 10,470,366 | B2 | 11/2019 | Mahien et al. |
| 2015/0264864 | A1 | 9/2015 | Branch et al. |
| 2017/0142900 | A1 | 5/2017 | Mahieu et al. |
| 2018/0168094 | A1* | 6/2018 | Koch ........................ G01J 5/07 |
| 2018/0310474 | A1* | 11/2018 | Posselius ............. A01D 41/127 |
| 2020/0113113 | A1* | 4/2020 | Shearer ................ A01B 49/027 |
| 2020/0120869 | A1 | 4/2020 | Vaudike et al. |
| 2020/0128733 | A1* | 4/2020 | Vandike ................. A01D 33/08 |
| 2021/0127573 | A1* | 5/2021 | Mahieu ............. A01D 41/1243 |

FOREIGN PATENT DOCUMENTS

WO WO-2018162699 A1 * 9/2018 ......... A01D 41/1243

* cited by examiner

*Primary Examiner* — Jelani A Smith

(57) ABSTRACT

A method of measuring residue ejected from an agricultural machine as the agricultural machine harvests a field includes transmitting an electromagnetic pulse toward a volume generally rearward of the agricultural machine, measuring a reflection of the electromagnetic pulse, calculating a property of residue ejected from the agricultural machine based on the measured reflection of the electromagnetic pulse, calculating a location at which the residue is expected to land in the field, and generating a residue map correlating an amount of residue with locations in the field.

20 Claims, 4 Drawing Sheets

METHODS OF MEASURING RESIDUE DURING HARVEST

CROSS-REFERENCE TO RELATED APPLICATIONS

This application claims the benefit of the filing date of U.S. Provisional Patent Application 63/045,308, filed Jun. 29, 2020, the entire disclosure of which is incorporated herein by reference.

FIELD

Embodiments of the present disclosure relate generally to machines and methods of harvesting crops. In particular, embodiments relate to methods and apparatus for characterizing residue spread from a combine harvester.

BACKGROUND

Self-propelled combine harvesters are used by farmers to harvest a wide range of crops. Typically, a combine harvester cuts crop material, threshes grain therefrom, separates the threshed grain from the straw, and cleans the grain before storage in an onboard tank. Straw and crop residue is ejected from the rear of the combine harvester in the field.

Combine harvesters typically include a cleaning unit to separate grain and chaff (also referred to in the art as material other than grain (MOG)). The cleaned grain is conveyed to a discharge auger that elevates the grain to an onboard storage bin, whereas MOG and possibly unthreshed grain are directed over the edge of a bottom sieve assembly to a different discharge outlet for recirculation back through the thresher rotor assembly and cleaning system to extract any unthreshed grain. A fan of the cleaning system produces an airstream through the cleaning system that entrains the lighter non-grain particles and carries them out the rear of the combine harvester. Combine harvesters may include spreading mechanisms, such as described in U.S. Pat. No. 4,637,406, "Chaff and straw spreading attachment for combines," granted Jan. 20, 1987; and U.S. Pat. No. 5,569,081, "Distributing device for chopper," granted Oct. 29, 1996.

Because residue can be spread in different patterns based on wind and field conditions (e.g., slope, crop density, etc.), sensors may be placed on combine harvesters to determine the spread of residue. Information from the sensors may be used to adjust operating parameters of the spreading mechanisms to achieve a selected residue distribution. Such sensors are described in more detail in U.S. Patent Application Publication 2015/0264864, "MOG sensing system for a residue spreader," published Sep. 24, 2015; U.S. Patent Application Publication 2017/0142900, "Monitoring system for an agricultural harvester and agricultural harvester," published May 25, 2017; and U.S. Pat. No. 10,470,366, "Residue spreading system," granted Nov. 12, 2019.

BRIEF SUMMARY

In some embodiments, a method of measuring residue ejected from an agricultural machine as the agricultural machine harvests a field includes transmitting an electromagnetic pulse toward a volume generally rearward of the agricultural machine, measuring a reflection of the electromagnetic pulse, calculating a property of residue ejected from the agricultural machine based on the measured reflection of the electromagnetic pulse, calculating a location at which the residue is expected to land in the field, and generating a residue map correlating an amount of residue with locations in the field.

BRIEF DESCRIPTION OF THE DRAWINGS

While the specification concludes with claims particularly pointing out and distinctly claiming what are regarded as embodiments of the present disclosure, various features and advantages of embodiments of the disclosure may be more readily ascertained from the following description of example embodiments of the disclosure when read in conjunction with the accompanying drawings, in which:

DETAILED DESCRIPTION

Figure 1:
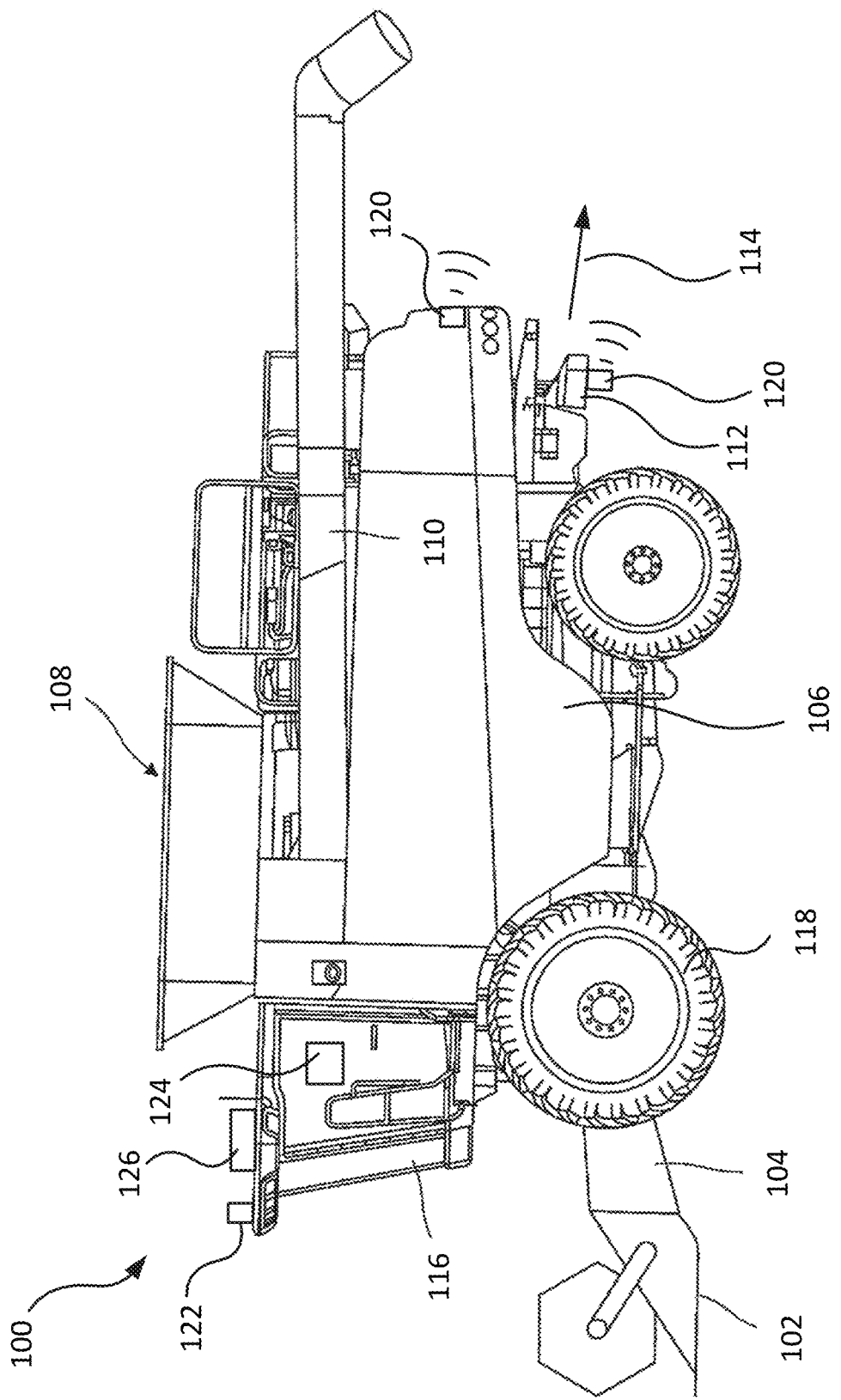
FIG. 1 is a simplified side view of a combine harvester.

The illustrations presented herein are not actual views of any particular machine or portion thereof, but are merely idealized representations employed to describe example embodiments of the present disclosure. Additionally, elements common between figures may retain the same numerical designation.

The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, the description provided below does not include all elements to form a complete structure or assembly. Only those process acts and structures necessary to understand the embodiments of the disclosure are described in detail below. Additional conventional acts and structures may be used. Also note, the drawings accompanying the application are for illustrative purposes only, and are thus not drawn to scale.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other, compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter).

FIG. 1 illustrates an agricultural machine in the form of a self-propelled combine harvester 100 that carries a header 102, which cuts and gathers a strip of crop as the combine harvester 100 is driven across a crop field. An elevator section 104 conveys the cut crop stream from the header 102 into a crop processing apparatus 106 in the combine harvester 100. Clean grain separated from the crop stream is collected in a storage tank 108, which is periodically emptied into a trailer or other vehicle or storage container via an unloading auger 110. Residue material remaining from the crop stream, such as straw and chaff, is ejected by a spreading system 112 from the rear of the combine harvester 100, represented by arrow 114. The combine harvester 100 also typically includes an operator cab 116, an engine, and wheels 118 and/or tracks. One or more sensors 120 may be configured to detect residue ejected from the spreading system 112 and traveling rearward and outward from spreading system 112.

The sensors 120 may be, for example, radar sensors configured to transmit electromagnetic pulses toward a volume generally rearward from the combine harvester 100 (e.g., directly behind the combine harvester 100 as well as to either side of the spreading system 112). In some embodiments, the sensors 120 may transmit electromagnetic pulses over an angle of at least 140°, at least 170°, or even at least 180° from the rear of the combine harvester 100. The sensors 120 may be configured to measure a reflection of the electromagnetic pulse, and in so doing, infer the position (e.g., azimuth angle and distance) of particles of material. The combine harvester 100 may typically have two or more sensors 120 arranged horizontally parallel to an axis of the header 102 along the rear of the combine harvester 100. In other embodiments and as shown in FIG. 1, the combine harvester 100 may carry sensors 120 at different heights from the ground.

Information from the sensors 120 may be used to calculate a property of the residue ejected from the combine harvester 100. For example, the sensor information may be used to calculate the residue mass, residue location, particle size distribution, residue velocity, etc.

The combine harvester 100 may also include a wind sensor 122 configured to detect wind speed. The wind sensor 122 may be in communication with a speed sensor of the combine harvester 100 so that the wind speed can be corrected based on ground speed of the combine harvester 100. In some embodiments, the sensors 120, 122 may communicate with a computer 124 on board the combine harvester 100, which may be located in the cab 116. Alternatively, the computer 124 may be located elsewhere, and may have a user interface in the cab 116. A GPS antenna 126 may be used by the computer 124 to determine the location of the combine harvester 100.

Figure 2:
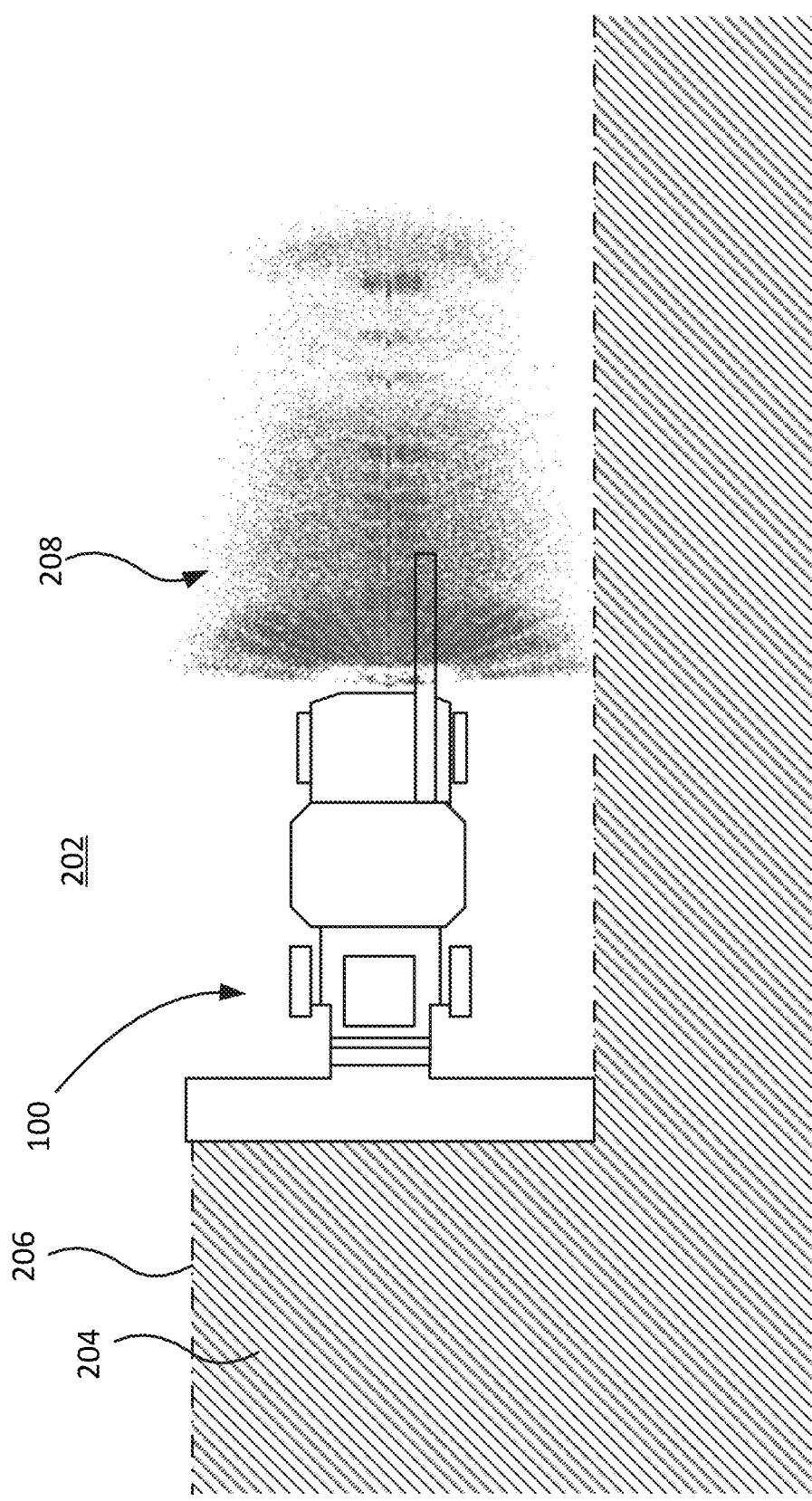
FIG. 2 is a simplified top view of the combine harvester of FIG. 1 harvesting an agricultural field.

FIG. 2 is a simplified top view of the combine harvester 100 shown in FIG. 1 harvesting a field. The field includes a harvested area 202 and an unharvested area 204, separated in FIG. 2 by a dashed line 206. As the combine harvester 100 travels through the field and harvests crops therein, the spreading system 112 distributes residue 208 in the field. Information from the sensors 120 and the GPS antenna 126 may be used by the computer 124 (FIG. 1) to determine the location of particles of residue traveling in the air, which may be visualized as shown in FIG. 2.

Particle velocity may be used as a filter to remove reflections from the ground from calculations of residue location. That is, if a pulse is determined to be reflected from mass having zero velocity, the computer 124 may infer that the pulse was reflected off the ground, and may ignore that pulse when calculating the properties of the residue 208.

The computer 124 may use the properties of the residue 208 (typically mass and location or velocity and location) in combination with ground speed and/or wind speed, to calculate the trajectory of the residue 208 and predict where the residue 208 will land. The computer 124 may also optionally adjust an operating parameter of the combine harvester 100 (e.g., a ground speed, an operating parameter of the header 102, an operating parameter of the crop processing apparatus 106, and/or an operating parameter of the spreading system 112). In other embodiments, the computer 124 may simply calculate the trajectory of the residue 208 without attempting to cause the combine harvester 100 to change where the residue 208 will land.

A person having ordinary skill in the art will recognize that the residue 208 is not a uniform or continuous object. Thus, as used herein, the properties and location of the residue 208 refer to distributions thereof in space and over the surface of the field, which distributions may have any selected size resolution based on measurement capabilities of the sensors 120, processing and storage capabilities of the computer 124, etc.

The computer 124 may integrate the predicted landing locations of the residue 208 to generate a residue map correlating an amount of residue with locations in the field. The resulting residue map may include a representation of the median particle size at a location, total mass per unit area, or any other selected property. A graphical representation of the residue map may be displayed as a color-coded representation on a display (e.g., a touchscreen) of the computer 124 in the cab 116. An operator of the combine harvester 100 may make adjustments based on the graphical representation to achieve a more desirable spread of the residue 208 on the ground. In some embodiments, the residue map may be used to generate an alert to the operator, along with a suggestion of changes to operating parameter(s) to improve residue distribution.

Even if no changes are made to the operation of the combine harvester 100 based on the residue map, the residue map may be used to prepare a prescription map of the field for a subsequent operation. Decomposition of the residue 208 typically changes the composition of the soil, and so variations in the amount of residue 208 at a different locations can cause variations in the soil in subsequent seasons, even if the soil was initially similar. Different amounts of nutrients (e.g., fertilizer), different amounts of soil preparation (e.g., tillage), and/or different planting parameters (e.g., seed spacing) may be used in subsequent agricultural operations to account for differences across the residue map. Any such differences fall within the meaning of the term "prescription map" as used herein. The prescription map may be generated using any available information, including the residue map, a terrain map, historical planting and harvest information, precipitation information, etc.

In some embodiments, the residue map may be transferred to another computer before generating the prescription. For example, the residue map may be transferred via a wireless network, a storage device (e.g., a flash drive, an optical disc, etc.), a wired network, etc. For example, the residue map may be transferred via the internet. The prescription map for subsequent agricultural operations may be generated by another computer remote from the combine harvester 100. In some embodiments, the residue map may be transferred after the combine harvester 100 completes harvest of an entire field. In other embodiments, the residue map may be continuously updated, and the updated portions may be transferred during the harvest. In yet other embodiments, multiple combine harvesters 100 may together harvest the field, and one or more of the combine harvesters 100 may collect data from the others to generate a single residue map.

In some embodiments, the residue map may be generated by a computer remote from the combine harvester 100. That is, data from the sensors 120, 122 may be transferred from the combine harvester 100 to a remote computer, and the remote computer may generate the residue map. The remote computer may also generate the subsequent prescription map. The remote computer may send information about the residue map or proposed changes to the operating parameters of the combine harvester 100 back to the combine harvester 100.

Figure 3:
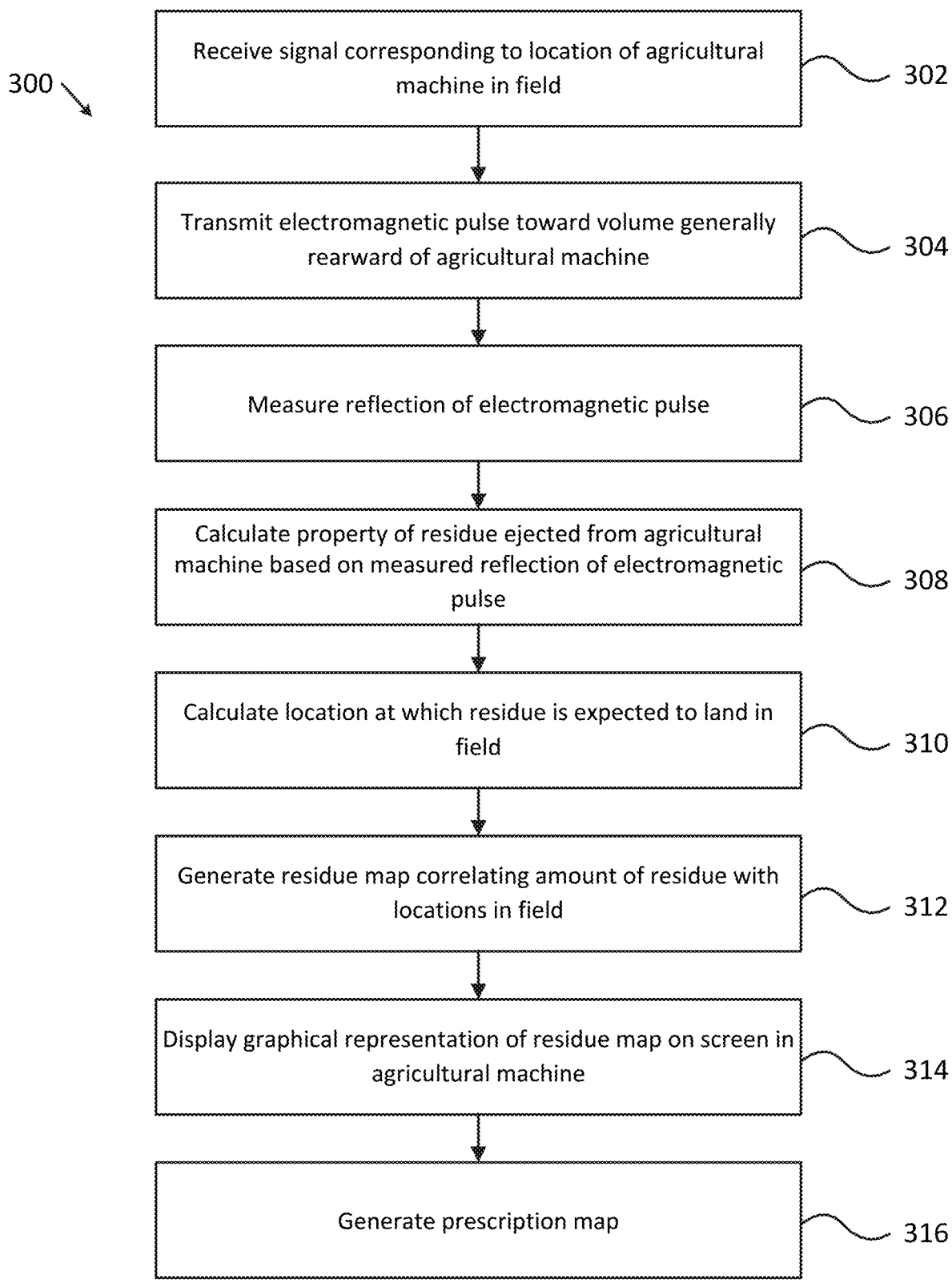
FIG. 3 is a simplified flow chart illustrating a method of measuring residue ejected from an agricultural machine during harvest.

FIG. 3 is a simplified flow chart illustrating a method 300 of measuring residue ejected from an agricultural machine as the agricultural machine harvests a field. In block 302, a signal is received corresponding to a location of the agricultural machine within the field (e.g., a GPS signal). In block 304, an electromagnetic pulse is transmitted toward a volume generally rearward of the agricultural machine. For example, electromagnetic pulses may be transmitted over an angle of about 180° from the rear of the machine. In block 306, a reflection of the electromagnetic pulse may be measured.

In block 308, a property of residue ejected from the agricultural machine may be calculated based on the measured reflection of the electromagnetic pulse. In block 310, a location at which the residue is expected to land may be calculated based on the property. In block 312, a residue map is generated to correlate the amount of residue with locations in the field. In block 314, a graphical representation of the residue map is displayed on a screen in the agricultural machine. In block 316, a prescription map is generated based on the residue map.

Though depicted as a flow chart, the actions in FIG. 3 may be performed concurrently, and in some embodiments, some actions may be omitted.

Figure 4:
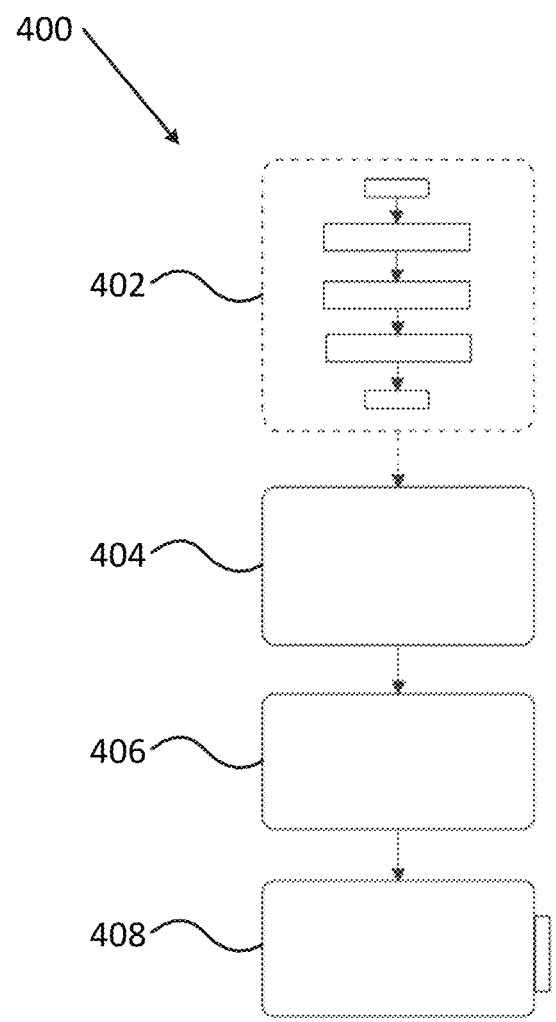
FIG. 4 illustrates an example computer-readable storage medium comprising processor-executable instructions configured to embody one or more of the methods of measuring residue, such as the method illustrated in FIG. 3.

Still other embodiments involve a computer-readable storage medium (e.g., a non-transitory computer-readable storage medium) having processor-executable instructions configured to implement one or more of the techniques presented herein. An example computer-readable medium that may be devised is illustrated in FIG. 4, wherein an implementation 400 includes a computer-readable storage medium 402 (e.g., a flash drive, CD-R, DVD-R, application-specific integrated circuit (ASIC), field-programmable gate array (FPGA), a platter of a hard disk drive, etc.), on which is computer-readable data 404. This computer-readable data 404 in turn includes a set of processor-executable instructions 406 configured to operate according to one or more of the principles set forth herein. In some embodiments, the processor-executable instructions 406 may be configured to cause a computer associated with the combine harvester 100 (FIG. 1) to perform operations 408 when executed via a processing unit, such as at least some of the example method 300 depicted in FIG. 3. In other embodiments, the processor-executable instructions 406 may be configured to implement a system, such as at least some of the example combine harvester 100 depicted in FIG. 1. Many such computer-readable media may be devised by those of ordinary skill in the art that are configured to operate in accordance with one or more of the techniques presented herein.

Additional non limiting example embodiments of the disclosure are described below.

Embodiment 1: A method of measuring residue ejected from an agricultural machine as the agricultural machine harvests a field. The method comprises transmitting an electromagnetic pulse toward a volume generally rearward of the agricultural machine, measuring a reflection of the electromagnetic pulse, calculating a property of residue ejected from the agricultural machine based on the measured reflection of the electromagnetic pulse, calculating a location at which the residue is expected to land in the field, and generating a residue map correlating an amount of residue with locations in the field.

Embodiment 2: The method of Embodiment 1, wherein calculating a location at which the residue is expected to land in the field comprises calculating an effect of wind on the residue.

Embodiment 3: The method of Embodiment 1 or Embodiment 2, further comprising displaying a graphical representation of the residue map on a display in the agricultural machine.

Embodiment 4: The method of Embodiment 3, wherein displaying a graphical representation of the residue map on a display in the agricultural machine comprises displaying a color-coded representation of the residue map on the display.

Embodiment 5: The method any one of Embodiment 1 through Embodiment 4, further comprising generating a prescription map based on the residue map after the agricultural machine harvests the field.

Embodiment 6: The method of Embodiment 5, wherein generating a prescription map comprises generating a map of nutrient amounts to be applied to the field.

Embodiment 7: The method of Embodiment 5, wherein generating a prescription map comprises generating a map of tillage settings to be used in tilling the field.

Embodiment 8: The method of Embodiment 5, wherein generating a prescription map comprises generating a map of seed spacing within the field.

Embodiment 9: The method of any one of Embodiment 1 through Embodiment 8, further comprising receiving a signal corresponding to a location of the agricultural machine in the field.

Embodiment 10: The method of any one of Embodiment 1 through Embodiment 9, further comprising transferring the residue map via wireless communication while the agricultural machine harvests the field.

Embodiment 11: The method of any one of Embodiment 1 through Embodiment 10, further comprising updating the residue map while the agricultural machine harvests the field.

Embodiment 12: The method of any one of Embodiment 1 through Embodiment 11, wherein calculating a property of the residue material comprises calculating a property selected from the group consisting of residue mass, residue location, particle size distribution, and residue velocity.

Embodiment 13: The method of any one of Embodiment 1 through Embodiment 12, further comprising adjusting an operating parameter of the agricultural machine based at least in part on the residue map.

Embodiment 14: The method of any one of Embodiment 1 through Embodiment 13, further comprising providing an operator with a notification to change an operating parameter of the agricultural machine based at least in part on the residue map.

Embodiment 15: A non-transitory computer-readable storage medium, the computer-readable storage medium including instructions that when executed by a computer, cause the computer to perform the method of any one of Embodiment 1 through Embodiment 14.

All references cited herein are incorporated herein in their entireties. If there is a conflict between definitions herein and in an incorporated reference, the definition herein shall control.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the invention as hereinafter claimed, including legal equivalents thereof. In addition, features from one embodiment may be combined with features of another embodiment while still being encompassed within the scope of the invention as contemplated by the inventors. Further, embodiments of the disclosure have utility with different and various crop-harvesting machine types and configurations.

What is claimed is:

1. A method of measuring residue ejected from an agricultural machine as the agricultural machine harvests a field, the method comprising:
    transmitting an electromagnetic pulse toward a volume generally rearward of the agricultural machine;
    measuring a reflection of the electromagnetic pulse;
    determining velocities of masses represented in the measured reflection;
    based at least partially on the determined velocities of the masses represented in the measured reflection, distinguishing reflections from ground from reflections from residue ejected from the agricultural machine;
    calculating a property of the residue ejected from the agricultural machine based on the measured reflections from the residue;
    calculating a location at which the residue is expected to land in the field; and
    generating a residue map correlating an amount of residue with locations in the field.

2. The method of claim 1, wherein calculating the location at which the residue is expected to land in the field comprises calculating an effect of wind on the residue.

3. The method of claim 1, further comprising displaying a graphical representation of the residue map on a display in the agricultural machine.

4. The method of claim 3, wherein displaying the graphical representation of the residue map on the display in the agricultural machine comprises displaying a color-coded representation of the residue map on the display.

5. The method of claim 1, further comprising generating a prescription map based on the residue map after the agricultural machine harvests the field.

6. The method of claim 5, wherein generating the prescription map comprises generating a map of nutrient amounts to be applied to the field.

7. The method of claim 5, wherein generating the prescription map comprises generating a map of tillage settings to be used in tilling the field.

8. The method of claim 5, wherein generating the prescription map comprises generating a map of seed spacing within the field.

9. The method of claim 1, further comprising receiving a signal corresponding to a location of the agricultural machine in the field.

10. The method of claim 1, further comprising transferring the residue map via wireless communication while the agricultural machine harvests the field.

11. The method of claim 1, further comprising updating the residue map while the agricultural machine harvests the field.

12. The method of claim 1, wherein calculating a property of the residue material comprises calculating a property selected from residue mass, residue location, particle size distribution, and residue velocity.

13. The method of claim 1, further comprising adjusting an operating parameter of the agricultural machine based at least in part on the residue map.

14. The method of claim 1, further comprising providing an operator with a notification to change an operating parameter of the agricultural machine based at least in part on the residue map.

15. A non-transitory computer-readable storage medium, the computer-readable storage medium including instructions that when executed by a computer, cause the computer to:
    cause a sensor to transmit an electromagnetic pulse toward a volume generally rearward of an agricultural machine;
    cause the sensor to measure a reflection of the electromagnetic pulse;
    determine velocities of masses represented in the measured reflection;
    based at least partially on the determined velocities of the masses represented in the measured reflection, distinguish reflections from ground from reflections from residue ejected from the agricultural machine;
    calculate a property of residue ejected from the agricultural machine based on the measured reflections from the residue;
    calculate a location at which the residue is expected to land in the field; and generate a residue map correlating an amount of residue with locations in the field.

16. The non-transitory computer-readable storage medium of claim 15, wherein the instructions further cause the computer to adjust an operating parameter of the agricultural machine based at least in part on the residue map.

17. The non-transitory computer-readable storage medium of claim 15, wherein the instructions further cause the computer to display a graphical representation of the residue map on a display in the agricultural machine.

18. The non-transitory computer-readable storage medium of claim 15, wherein the instructions further cause the computer to provide an operator of the agricultural machine with a notification to change an operating parameter of the agricultural machine.

19. The non-transitory computer-readable storage medium of claim 15, wherein the instructions further cause the computer to generate a prescription map based on the residue map after the agricultural machine harvests the field.

20. The non-transitory computer-readable storage medium of claim 15, wherein the instructions further cause the computer to transfer the residue map via wireless communication while the agricultural machine harvests the field.

* * * * *